United States Patent [19]

Haber et al.

[11] Patent Number: 4,710,170

[45] Date of Patent: Dec. 1, 1987

[54] ANTI-NEEDLE STRIKE AND ANTI-DRUG ABUSE SYRINGE

[75] Inventors: Terry M. Haber, Lake Forest; William H. Smedley, Lake Elsinore; Clark B. Foster, El Toro, all of Calif.

[73] Assignee: Habley Medical Technology Corporation, Laguna Hills, Calif.

[21] Appl. No.: 14,270

[22] Filed: Feb. 12, 1987

[51] Int. Cl.$^4$ .............................................. A61M 5/00
[52] U.S. Cl. .................................... 604/110; 604/195; 604/240
[58] Field of Search ............... 604/110, 111, 187, 192, 604/194, 195, 196, 197, 198, 240

[56] References Cited

U.S. PATENT DOCUMENTS

| 2,880,725 | 4/1959 | Kendall | 604/196 |
| 4,026,287 | 5/1977 | Haller | 604/195 |
| 4,507,117 | 3/1985 | Vinning et al. | 604/196 |
| 4,592,744 | 6/1986 | Jagger et al. | 604/192 |
| 4,634,428 | 1/1987 | Cuu | 604/110 |

Primary Examiner—John D. Yasko
Attorney, Agent, or Firm—Morland C. Fischer

[57] ABSTRACT

A disposable, anti-needle strike, anti-drug abuse syringe which reduces the frequency of accidental needle strikes to health care workers and prevents health-threatening reuse of the needle canula by drug abusers. The syringe has a needle carrying base and an attached hypodermic needle assembly which are relocatable within the syringe cylinder from a distally disposed first position to a proximally disposed second position. A piston assembly having a detachable stem moves reciprocally and axially through the syringe cylinder to expulse fluidic medication and to selectively engage the needle carrying base at the distal bore of the cylinder, whereby to relocate the needle carrying base and its attached needle assembly from the first position to the second position. The needle carrying base is anchored at the second position, such that the used needle extends into and is shielded by the syringe cylinder. The stem is then detached from the piston assembly and inserted through the now open orifice at the distal bore of the cylinder. The piston assembly stem is axially advanced through the syringe cylinder until contact is made with the needle canula which is anchored at and extended into the cylinder from the second cylinder position. The piston stem is further advanced to thereby bend, rather than unsafety snap, the needle canula. The stem is locked at its final position within the syringe cylinder to create a disposal cartridge with the needle canula destroyed, shielded and rendered irretrievable therewithin.

21 Claims, 19 Drawing Figures

ANTI-NEEDLE STRIKE AND ANTI-DRUG ABUSE SYRINGE

BACKGROUND OF THE INVENTION

1. FIELD OF THE INVENTION

This invention relates to a disposable hypodermic syringe which is adapted to reduce the frequency of accidental and, in some cases, life threatening, needle strikes while reducing instances of possible drug abuse by preventing reuse of the syringe needle by drug abusers.

2. PRIOR ART

Hypodermic syringes are used for a variety of injection procedures including the delivery of medicinal drugs to a recipient. However, once the injection procedure is completed and the syringe cylinder emptied, problems may arise as a consequence of failing to properly and adequately dispose of the syringe. By way of a first example, the syringe may be used to treat a patient having a communicable disease. To prevent reuse, the hypodermic needle is sometimes broken before the syringe is discarded. Health care workers are susceptible to accidental and potentially infectious needle strikes due to the careless handling of the hypodermic needle when breaking the needle or disposing of the syringe after use. The resulting mini-accidents caused by an accidental needle strike typically require a blood test for such disease as AIDS and hepatitis. The corresponding cost and inefficiency of testing health care workers who have received an inadvertent needle strike results in considerable waste, which may be particularly damaging to a health care facility striving for economy and efficiency.

By way of second example, drug addicts have been known to rummage through the trash of a health facility in an effort to find emptied syringes which have been discarded after use. Such syringes are often reused in an illicit capacity, whereby to promote drug abuse and the possible spread of contagious disease among drug users. Unfortunately, no disposable syringe is presently known which includes means to reliably reduce the frequency of accidental needle strikes suffered by health care workers while preventing reuse of the syringe by drug users.

SUMMARY OF THE INVENTION

In general terms, a disposable, anti-needle strike and anti-drug abuse syringe is disclosed which overcomes the problems inherent in a conventional syringe by reliably reducing the frequency of accidental needle strikes among health care workers while preventing reuse of the needle by drug abusers. The syringe includes a conventional hypodermic needle and luer lock assembly which is connected to and supported from a needle carrier base. The needle carrier base is removably attached to a first end of the syringe cylinder, such that the needle projects outwardly therefrom for injecting a fluid from the cylinder in the conventional manner.

The syringe also includes a piston assembly comprising the detachable connection of an elongated piston stem to a seal and lock assembly. A torroidal seal, formed at one end of the seal and lock assembly, functions as a plunger when the piston assembly is moved axially through the syringe cylinder during a fluid injection procedure. The torroidal seal has a receptacle formed therein at which the seal and lock assembly is adapted to selectively engage the needle carrier base when the piston assembly is moved to the first end of the syringe cylinder. The piston assembly is then moved away from the first cylinder end, whereby to remove the needle carrier base and the attached hypodermic needle from the first to an opposite end of the cylinder. The needle carrier base is anchored at the opposite cylinder end, such that the hypodermic needle extends into and is shielded by the syringe cylinder.

The piston stem is detached from the piston assembly by bending the stem relative to the seal and lock assembly. The piston stem is then inserted through an orifice at the first end of the syringe cylinder from which the needle carrier base was previously removed. The stem is axially advanced through the interior of the syringe cylinder towards the opposite end thereof until contact is made with the needle canula at the interior of the cylinder. The impact of the piston stem against the needle canula bends, rather than breaks, the needle within the cylinder. The piston stem is locked at its final position within the syringe cylinder to prevent access to or contact with the needle. The syringe may then be discarded in a normal fashion. However, by virtue of the present invention, the resulting cartridge is rendered safe by locking the hypodermic needle and needle carrier base within the syringe cylinder, so that the needle is shielded by the syringe cylinder. Accordingly, the used syringe is in a condition to permit safe disposal within requiring handling or cutting of the needle as has heretofore been necessitated as a consequence of conventional syringe assemblies.

DESCRIPTION OF THE PREFERRED EMBODIMENT

Figure 1:
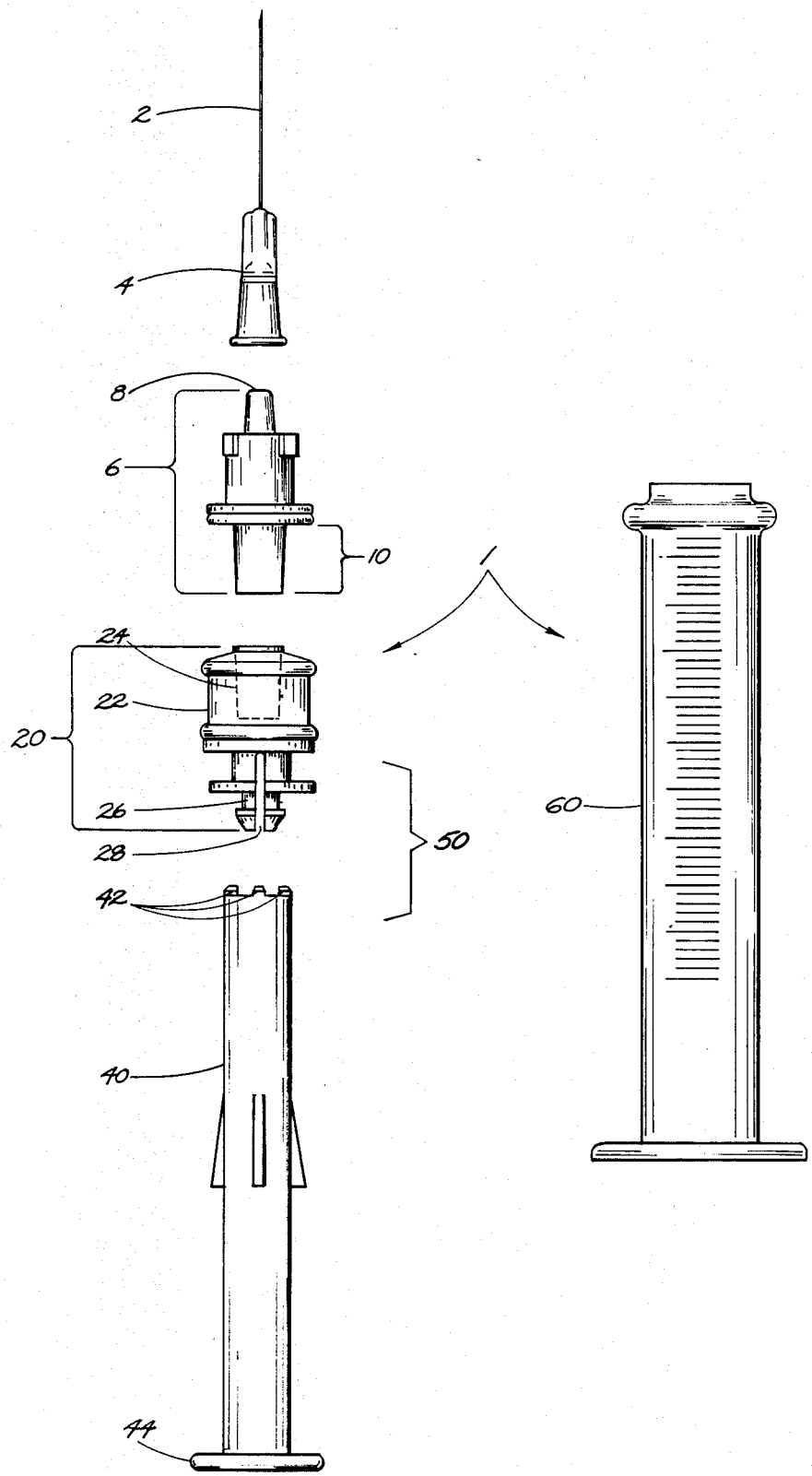
FIG. 1 is an exploded view of the anti-needle strike, anti-drug abuse syringe which forms the present invention.

The anti-needle strike and anti-drug abuse syringe which forms the present invention is best described while referring to the drawings. In FIG. 1, there is shown an exploded view of the syringe 1 with the syringe cylinder 60 removed. Details of the syringe cylinder 60 will be provided when referring to FIGS. 7–8 of the drawings. The syringe 1 includes a conventional hypodermic needle 2 supported by and projecting outwardly from a conventional hollow luer lock 4. A needle carrier base 6 has a luer lock receptacle 8 formed at a proximal end thereof for receiving the luer lock 4. A tapered stem 10 is formed at the opposite end of the carrier base 6. Additional details of needle carrier base 6 will be disclosed when referring to FIG. 3 of the drawings.

A seal and lock assembly 20 has a torroidal seal member 22 located at a distal end thereof. Formed within the seal member 22 is a hollow, tapered receptacle 24 which is sized to receive therewithin the tapered stem 10 of needle carrier base 6. One or more (e.g. four) locking fingers 26 extend outwardly from the proximal end of seal and lock assembly 20. Deflection slots 28 are formed between each pair of locking fingers 26. Additional details of the seal and lock assembly 20 will be disclosed when referring to FIGS. 4 and 5 of the drawings.

A cylindrical piston stem 40 correspondingly has one or more (e.g. four) teeth 42 formed at the distal end thereof. In the assembled syringe relationship shown in FIG. 2, each tooth 42 is aligned with a respective deflection slot 28 between pairs of locking fingers 26 of the seal and lock assembly 20, such that the stem 40 is snapped into releasable engagement with the seal and lock assembly 20 to form a piston assembly 50. A flange 44 is formed at the proximal end of stem 40. Additional details of the piston assembly stem 40 will be disclosed when referring to FIG. 6 of the drawings.

Figure 2:
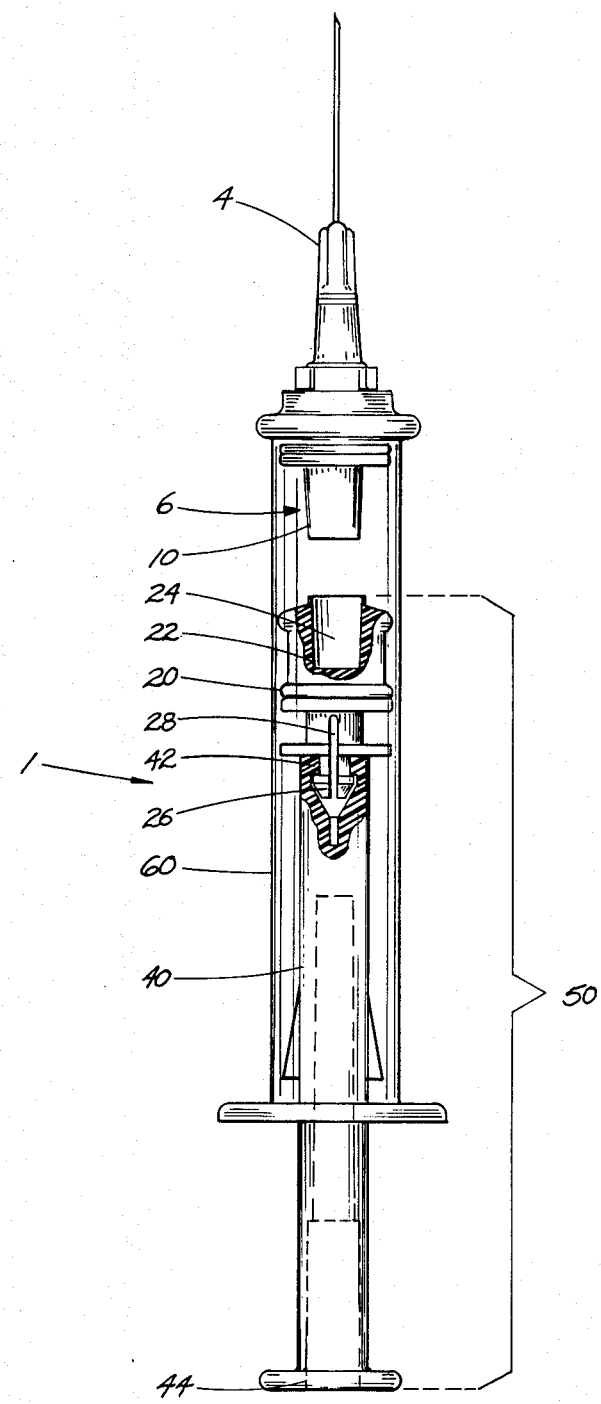
FIG. 2 illustrates the syringe of FIG. 1 in the assembled relationship.

The arrangement of the needle supporting luer lock 4, needle carrier base 6, seal and lock assembly 20, piston stem 40 and cylinder 60 to form the anti-needle strike and anti-drug abuse syringe 1 of this invention is best illustrated in FIG. 2 of the drawings. As previously indicated, the seal and lock assembly 20 and stem 40 are detachably snapped together to form a piston assembly 50 when locking teeth 42 of stem 40 are aligned with respective deflections slots 28 between locking fingers 26. Piston assembly 50 is adapted for axial and reciprocal movement through the syringe cylinder 60 so that a suitable fluid may be either infused from a supply thereof or expulsed from the cylinder 6 by way of a fluid path established through the needle carrier base 6 and hypodermic needle 2. When moved completely through the cylinder 60 to the most distal aspect thereof, the piston assembly 50 can be selectively mated to the needle carrier base 6 by depressing the piston assembly 50 at stem flange 44, such that the hollow tapered receptacle 24 of seal and lock assembly 20 surrounds the tapered stem 10 of the needle carrier base 6, for the purpose which will soon be described.

Figure 3:
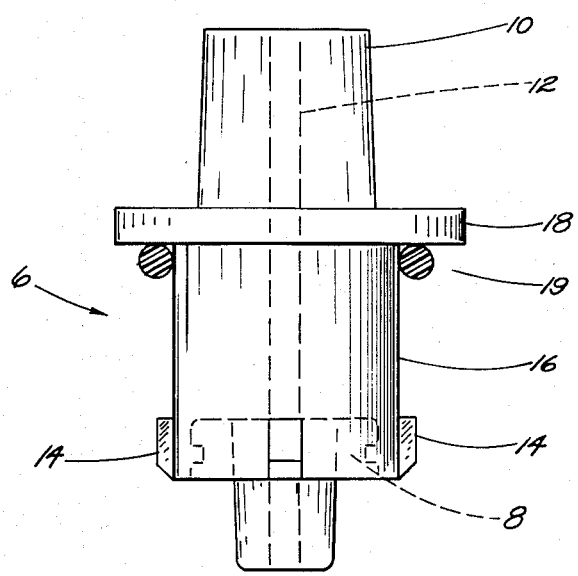
FIG. 3 is a side view of the needle carrier base which forms the syringe of FIG. 1.

FIG. 3 of the drawings shows a detailed enlargement of the needle carrier base 6 which was briefly described when referring to FIG. 1. A fluid passage 12 is formed through the needle carrier base 6 to permit fluid communication between the syringe cylinder and the hypodermic needle. As earlier indicated, the needle carrier base 6 includes a male luer lock receptacle 8 formed at the distal end thereof to receive the hypodermic needle supporting female luer lock 4. The needle carrier base 6 also includes a cylindrical barrel portion 16 formed between a luer lock receptacle 8 and a coextensively formed flange 18. An elastomeric sealing ring 19 is extended around barrel portion 16 and seated upon the flange 18. In the assembled relationship, the needle carrier base 6 is located within a bore at the most distal aspect of the syringe cylinder, such that the most distal aspect of barrel portion 16 and the luer lock receptacle 8 extend outwardly from the syringe cylinder and the flange 18 is positioned adjacent an internal sealing ring surface (designated 74 in FIG. 7) of the cylinder. The sealing ring 19 is thereby compressed between the flange 18 and the sealing ring surface to permit efficient flow of fluid through fluid path 12 and prevent leakage of fluid from the syringe cylinder at the interface with the barrel portion 16.

Extending radially outward around the periphery of the cylindrical barrel portion 16 is a plurality (e.g. three) of bayonet teeth 14. The teeth 14 are positioned 120° apart and are sized to be received within respective slots formed in the distal end of the syringe cylinder. The receipt of the bayonet teeth 14 through the slots of the syringe cylinder (as will be best described when referring to FIGS. 7–9) enables the needle carrier base 6 to be releasably secured to and fluid sealed against the syringe cylinder.

As also earlier disclosed, the needle carrier base 6 includes a tapered proximal end 10 disposed opposite luer lock receptacle 8. The tapered proximal end 10 (which tapers inwardly at an angle of approximately 2°) is coextensively connected to the barrel portion 16 at the flange 18. Tapered stem 10 is shaped so as to be received by a correspondingly shaped receptacle 24 formed in the seal and lock assembly (20 in FIG. 1) when the piston assembly (50 in FIG. 2) is moved axially through the syringe cylinder to the most distal aspect thereof, as will soon be explained.

Figure 4:
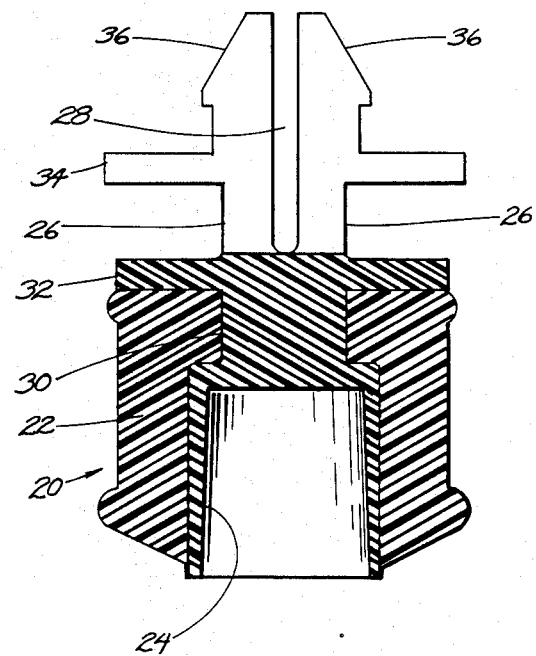
FIG. 4 is a side view of the seal and lock assembly which forms the syringe of FIG. 1.

FIG. 4 of the drawings shows a detailed enlargement of the seal and lock assembly 20 which was briefly described when previously referring to FIG. 1. As earlier indicated, seal and lock assembly 20 has a torroidal seal 22 located at the distal end thereof. The seal 22 is preferably formed form a suitable biomeric elastomer and is mounted upon a seal support stem 30. The torroidal seal 22 is snugly received within the syringe cylinder and forms a piston head (i.e. or plunger) when the seal and lock assembly 20 is snapped into connection with the piston stem to form the piston assembly (designated 50 in FIG. 2).

The seal support stem 30 is concentrically aligned with and surrounds the hollow receptacle 24 in which the tapered stem of needle carrier base 6 is received when the piston assembly is moved through the syringe cylinder 60 to the most distal aspect thereof. The walls of receptacle 24 are slightly tapered (at an angle of approximately 2°) to correspond with the taper of the stem 10 (of needle carrier base 6 of FIG. 3). The seal support stem 30 has a coextensively formed flange 32 against which the torroidal seal 22 is seated. Flange 32 applies sufficient force upon the seal 22 to move the seal and its internal receptacle 24 into engagement with the tapered stem of the needle carrier base 6 when the piston assembly is moved to the distal end of syringe cylinder 60. The receipt of tapered stem 10 within hollow receptacle 24 permits a reliable axial connection between the seal and lock assembly 20 and the needle carrier base 6 and the efficient transmission of torque therebetween.

Located at the proximal end of seal and lock assembly 20 are the locking fingers 26. Locking fingers 26 are preferably formed from a flexible, biocompatible thermoplastic material, such as an acetal homopolymer. The locking fingers 26 extend outwardly and axially from the flange 32 and are separated from one another by the axially aligned deflection slots 28. A coextensive, disk-like locking skirt 34 extends around the periphery of the locking fingers 26. Each of the locking fingers 26 terminates at a relatively large terminal 36 which projects from the locking skirt 34. The locking finger terminals 36 are separated from one another by respective locking slots 38 which extend radially through skirt 34 (of FIG. 5). The locking slots 38 formed in locking skirt 34 are separated from one another by approximately 120°. As will soon be explained, the enlarged terminals 36 of locking fingers 26 are received within the piston stem 40 (of FIG. 6) so that the seal and lock assembly 20 and the stem 40 can be detachably snapped together to form the piston assembly (designated 50 in FIG. 2).

Figure 6:
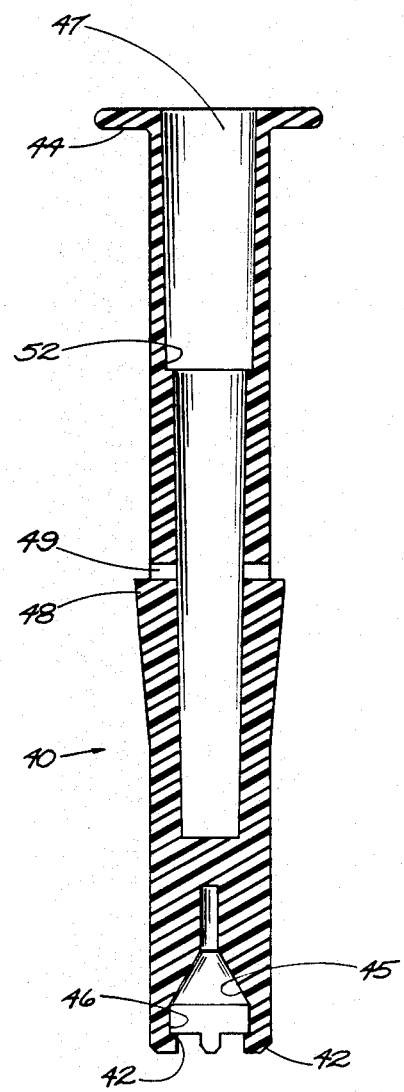
FIG. 6 is a cross-section of the piston assembly stem which forms the syringe of FIG. 1.

More particularly, FIG. 6 of the drawings shows a detailed enlargement of the cylindrical stem 40 which is interconnected to the seal and lock assembly 20 of FIG. 4 to form piston assembly 50. Located at the interior of the distal end of stem 40 is a tapered needle point receptacle 45 into which the distal point of the hypodermic needle canula will be guided to bend and destroy the canula after the syringe cylinder has been emptied. Projecting from the distal end of stem 40 are a plurality (e.g. four) of longitudinally extending teeth 42. An internal flange 46 is formed at the interface of the teeth 42 with the needle point receptacle 45.

Figure 5:
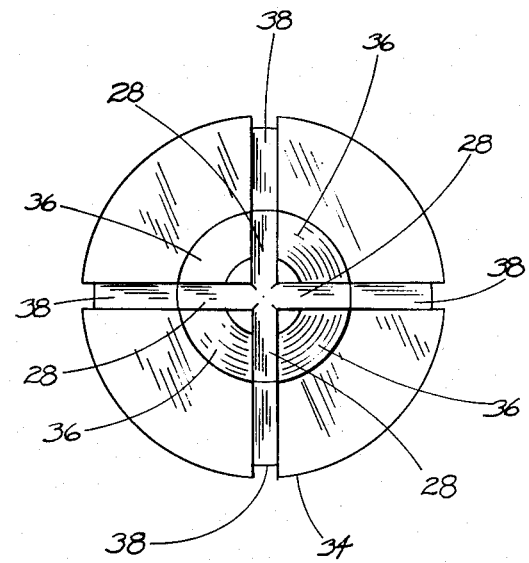
FIG. 5 is a top view of the seal and lock assembly of FIG. 4.

The detachable connection of the stem 40 and seal and lock assembly 20 to form the piston assembly is described while referring concurrently to FIGS. 4–6 of the drawings. The distal end of stem 40 is attached to the proximal end of seal and lock assembly 20, such that the enlarged terminals 36 of flexible locking fingers 26 are received within the receptacle 45, and the longitudinally extending locking teeth 42 are snapped into respective radially extending locking slots 38 formed in the locking skirt 34. That is to say, the engagement of the enlarged terminals 36 of seal and lock assembly 20 by the receptacle 45 of stem 40 bends the locking fingers 26 inwardly, until terminals 36 are located below the internal flange 46 of stem 40. The spring-like resilience of flexible locking fingers 26 and the location of terminals 36 below internal flange 46 prevents an inadvertent separation of the stem 40 from the seal and lock assembly 20 when the piston assembly is moved axially and reciprocally through the syringe cylinder.

When the seal and lock assembly 20 and stem 40 are detachably connected together, the resultant elongated piston assembly 50 is adapted to withstand an axially directed force (for moving the piston assembly through the syringe cylinder) but not a bending or torquing force. Therefore, by exerting a bending force upon the stem 40, the terminals 36 are pulled out of engagement with the receptacle 45 and the teeth 42 are removed from locking slots 38, whereby the stem 40 and seal and lock assembly 20 are separated from one another.

Referring once again to FIG. 6, an optional, elongated needle storage chamber 47 is formed at the proximal end of stem 40. For purposes of convenience, a combination hypodermic needle and luer lock (such as that designated 2 and 4 in FIG. 1) may be nested within chamber 37 and supported from an internal ledge 52 to permit ready access thereto by the physician. The inclusion of needle storage chamber 47 within stem 40 advantageously eliminates the added cost for separate packaging and sterilization of the hypodermic needle, while assuring that a needle is conveniently and readily available at the time during which the syringe is to be used.

A flexible locking catch 48 is coextensively formed with and extended radially outward from the cylindrical body of piston stem 40. Locking catch 48 is surrounded by a recess 49 formed within stem 40. Although only a single locking catch 48 and recess 49 are illustrated, it is to be understood that a plurality of axially aligned catches and recesses may be formed along the body of stem 40. The flexible locking catch 48 is adapted to prevent the removal of stem 40 from the distal end of the syringe cylinder by locking the stem within the cylinder when the stem is inserted through the distal cylinder end for a purpose and in a manner that will be disclosed in greater detail hereinafter.

Figure 7:
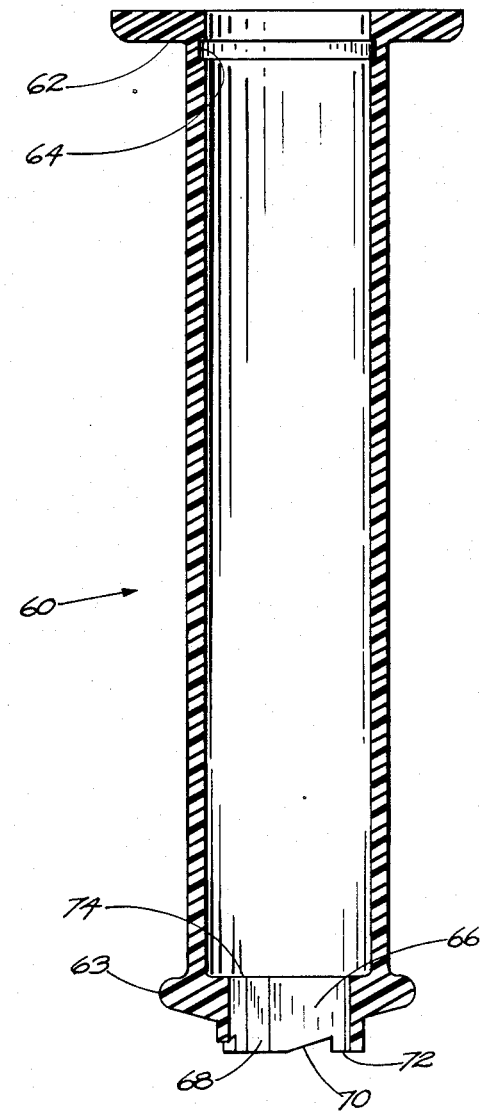
FIG. 7 is a cross-section of the cylinder which forms the syringe of FIG. 1.
Figure 8:
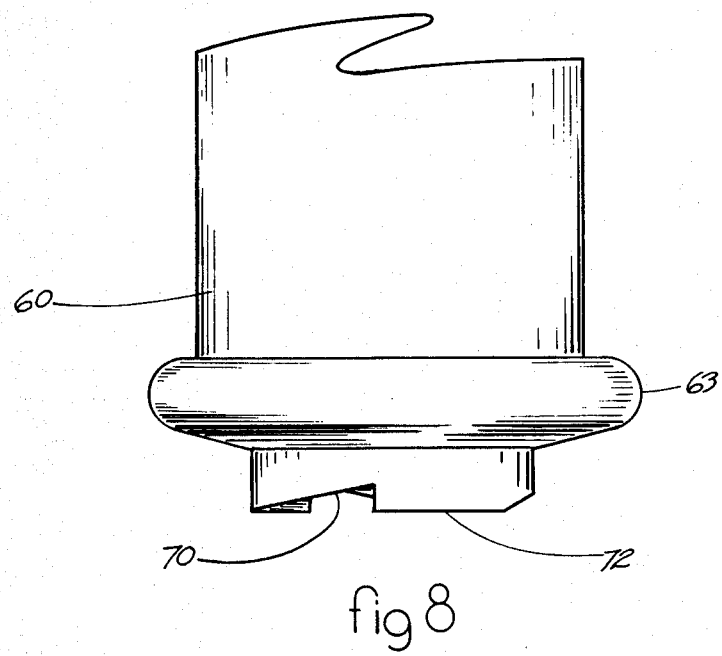
FIG. 8 is a partial side view of the syringe cylinder of FIG. 7.
Figure 9:
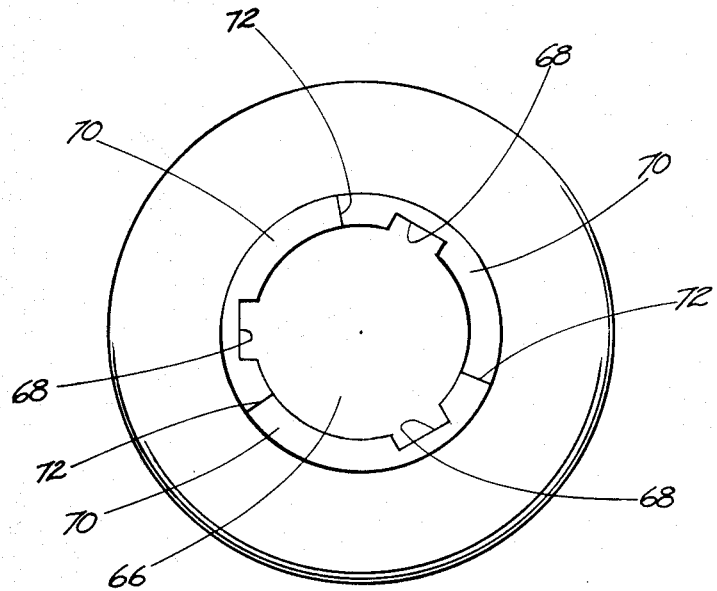
FIG. 9 is a bottom view of the syringe cylinder of FIG. 8.

FIGS. 7–9 of the drawings show a detailed enlargement of the cylindrical syringe cylinder 60 through which the piston assembly 50 (of FIG. 2) is axially and reciprocally moved. Syringe cylinder 60 is fabricated from a clear, plastic material, or the like, and is provided with incremental markings as is common to a conventional linear or plunger-type syringe. Cylinder 60 has a coextensively formed major flange 62 around the most proximal aspect thereof. An anti-slip flange 63 is formed around the distal cylinder end. The proximal end of cylinder 60 is open in order that the seal and lock assembly 20 (of FIG. 4) can be moved therethrough and located at the interior of the cylinder. Extending around the open proximal end of syringe cylinder 60 is an internal locking groove 64 (best shown in FIG. 7). The locking groove 64 has a slightly larger diameter than the open proximal end of cylinder 60. The groove 64 is sized to receive therewithin and anchor the locking skirt (34 in FIG. 4) of the seal and lock assembly 20 (in FIG. 4) when such assembly is relocated through the syringe cylinder 60 to the most proximal aspect thereof. The retaining and anchoring of locking skirt 34 within locking groove 64 prevents the removal of the seal and lock assembly and blocks access to the interior of the cylinder 60 via the proximal end thereof. Moreover, the groove 64 also facilitates the disassembly of the piston assembly (50 in FIG. 2) and the detachment of the stem (40 in FIG. 6) from the seal and lock assembly 20 by anchoring the seal and lock assembly and enabling stem 40 to be bent relative to locking skirt 34, as will soon be described in greater detail.

The detail end of syringe cylinder 60 is also open to retain therewithin the needle carrier base 6 (of FIG. 3) from which the hypodermic needle is supported. More particularly, and referring concurrently to FIGS. 3 and 7–9, the distal cylinder end includes a centrally disposed bore 66. Located around the periphery of bore 66 are a plurality (e.g. three) of notches 68. Each notch is sized and aligned to receive therethrough a respective bayonet tooth 14 of the needle carrier base 6. Shallow ramp portions 70 are formed between each pair of notches 68. An end wall 72 is formed at the bottom of each ramp portion 70.

To connect the needle carrier base 6 to the syringe cylinder 60, the needle carrier base is pushed through the open proximal end of the cylinder 60 and moved axially through the cylinder body to the bore 60 formed at the distal cylinder end, such that the bayonet teeth 14 of the needle carrier base 6 are received in respective notches 68. The needle carrier base 6 is then rotated in a clockwise direction, whereby the teeth 14 will be correspondingly displaced down the ramp portions 70 and into engagement with the end walls 72. The abutment of the teeth 14 against the end wall 72 prevents any further rotation of needle carrier base 6. The displacement of the teeth 14 away from the notches 68 and down the ramps 70 cams the needle carrier base 6 slightly forward in the syringe cylinder to securely attach carrier 6 to cylinder 60 and prevents the inadvertent removal of the carrier base 6 from the distal cylinder end. An internal sealing ring surface 74 is formed around syringe cylinder 60 below the bore 66 thereof to engage the elastomeric sealing ring 19 of needle carrier base 6 and form a fluid-tight seal therebetween.

The needle carrier base 6 is released from the distal bore 66 of cylinder 60 by rotating the carrier base in a counter-clockwise direction, so that the bayonet teeth thereof are moved up the ramp portions 70 and back into alignment with the notches 68. The needle carrier base 6 may then be relocated from the distal to the proximal end of the cylinder in a manner and for a purpose which will now be described.

Figure 10:
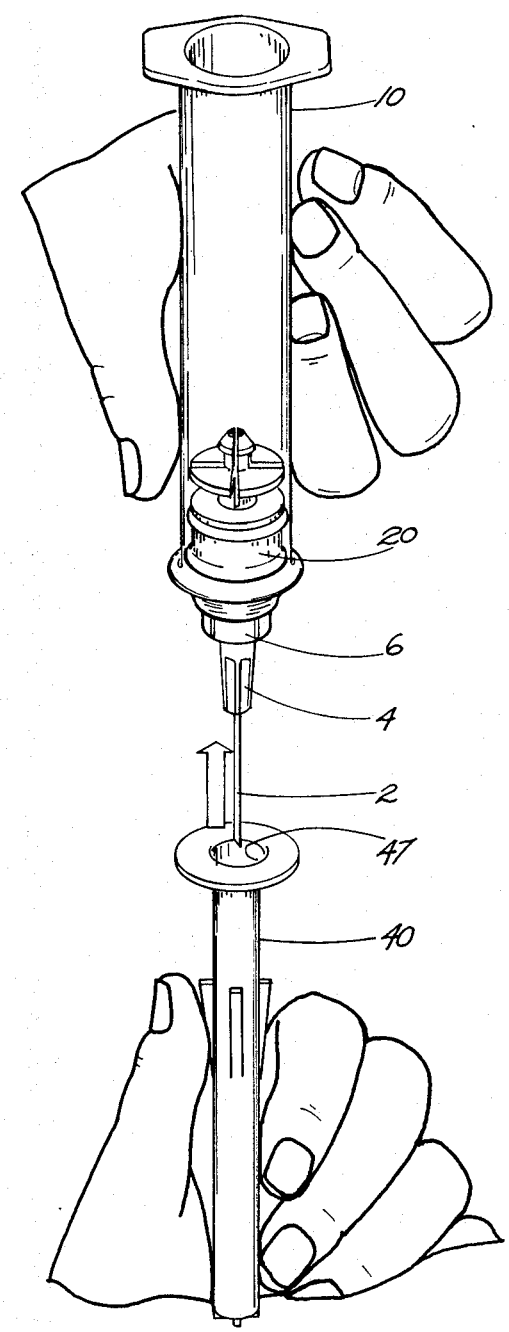
FIGS. 10–17 illustrate the operating procedure of the syringe of FIG. 1.

The operation of the anti-needle strike and anti-drug abuse syringe is now described while referring to FIGS. 10–17 of the drawings. Referring initially to FIG. 10, the needle carrier base 6 is first secured to the distal end of the syringe cylinder 60 and the seal and lock assembly 20 is mated to the needle carrier base 6 in the manner previously described. The hypodermic needle 2 and associated luer lock 4 are then removed from the packaging nest within the needle storage chamber 47 of piston stem 40 and attached to the needle carrier base 6. The foregoing is accomplished by moving the distal end of cylinder 60 to which is attached the needle carrier base 6 into contact with the luer lock 4 at needle storage chamber 47. The syringe cylinder 60 is rotated slightly so that the luer lock 4 is engaged by and attached to the needle carrier base 6. The syringe cylinder 60 is then moved away from the piston stem 40 (in the direction of the reference arrow) such that the attached hypodermic needle 2 and luer lock 4 are withdrawn from needle storage chamber 47.

Figure 11:
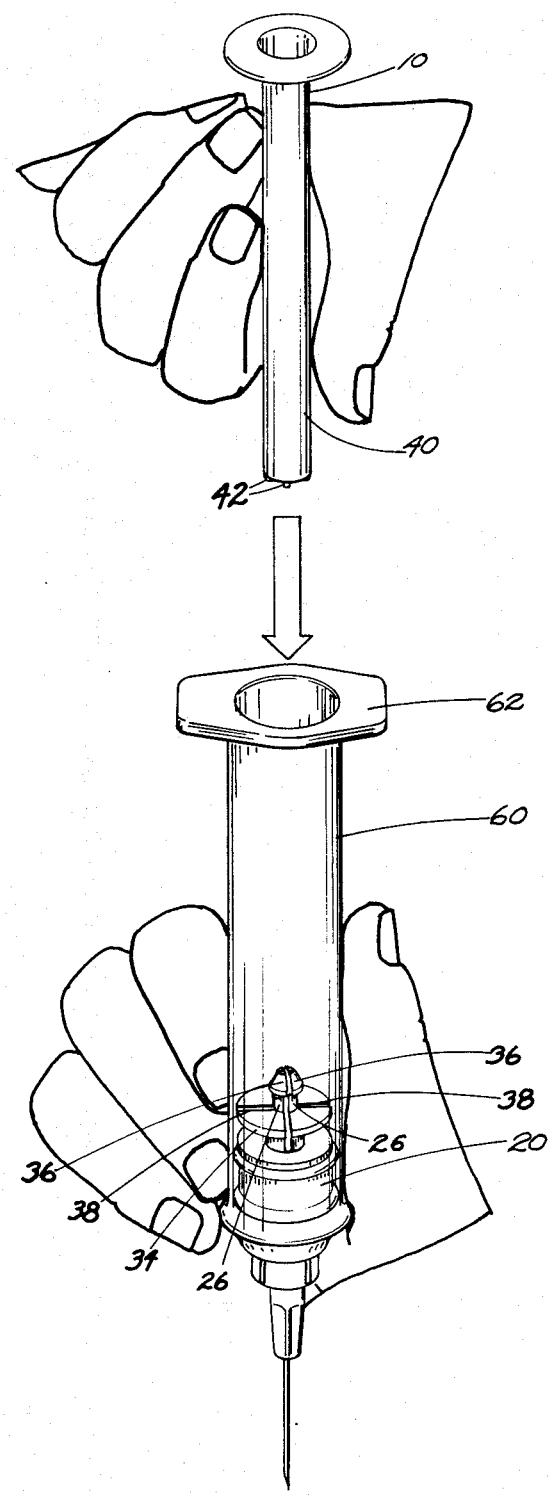

In FIG. 11, the piston assembly 50 is completed by inserting the piston stem 40 past major flange 62 and through the open proximal end of syringe cylinder 60 to detachably connect stem 40 to seal and lock assembly 20 at the interior of the cylinder 60. That is, and as was previously disclosed while referring to FIGS. 4–6, the locking teeth 42 of stem 40 are snapped into the radial locking slots 38 formed in the locking skirt 34 of seal and lock assembly 20, and the terminals 36 of the locking fingers 26 are retained within the needle point receptacle (45 in FIG. 6) at the interior of stem 40.

Figure 12:
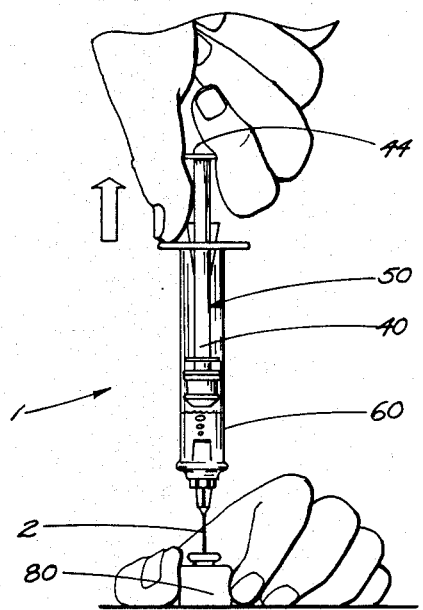

In FIG. 12, the hypodermic needle 2 is moved into fluid communication with a fluid drug supply 80, or the like. Accordingly, the syringe 1 is infused with the fluid medication from the supply 80 thereof in a conventional manner by grasping flange 44 of piston stem 40 and pulling the piston assembly 50 through syringe cylinder 60 in the direction of the reference arrow. The syringe 1 is now ready to execute a conventional injection procedure by depressing the flange 44 of piston stem 40 and driving the piston assembly 50 axially through syringe cylinder 60 in a direction opposite to that shown by the reference arrow.

Figure 13:
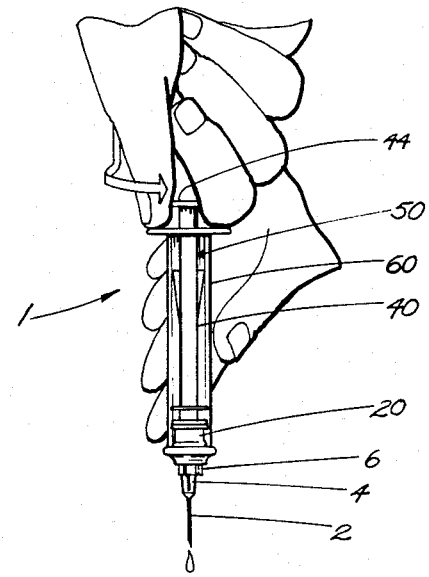

At the conclusion of the injection procedure, the piston assembly 50 in FIG. 13 is moved completely and axially through the syringe cylinder 60 until the seal and lock assembly 20 of piston assembly 50 is located at the most distal aspect of cylinder 60, whereby the tapered stem (10 in FIG. 3) of needle carrier base 6 is received within the receptacle (24 in FIG. 4) formed in a seal and lock assembly 20. Next, the flange 44 of piston assembly stem 40 is depressed to apply an axial force to needle carrier base 6 while the piston stem 40 is rotated (approximately 120°) in the counter-clockwise direction of the reference arrow. Rotating stem 40 while the seal and lock assembly 20 engages needle carrier base 6 transmits torque from the stem 40 to the needle carrier base which causes a corresponding rotation of the carrier base 6 and a displacement of the bayonet teeth (14 in FIG. 3) thereof. The bayonet teeth of needle carrier base 6 are moved up the ramps (70 in FIGS. 7–9) and aligned with the notches (68 in FIGS. 7 and 9) formed in the distal end of syringe cylinder 60.

Figure 14:
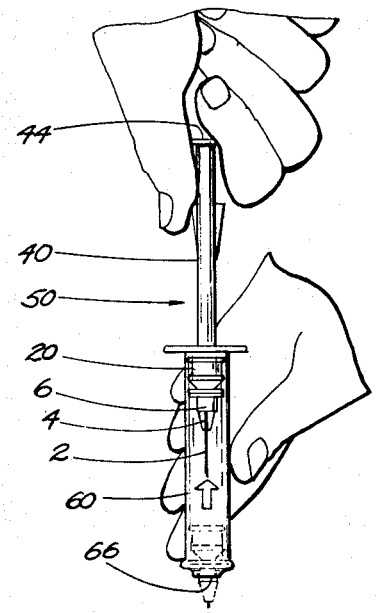

In FIG. 14, the needle carrier base 6 (with the hypodermic 2 and the luer lock 4 attached thereto) is removed from the bore 66 formed in the distal end of syringe cylinder 60. The flange 44 of piston stem 40 is grasped and the piston assembly 50 is pulled (in the direction of the reference arrow) axially outward through the syringe cylinder 60 from the proximal end thereof. More particularly, the stem 40 is withdrawn from the cylinder 60 until the locking skirt (34 in FIG. 4) of seal and lock assembly 20 is seated and anchored within the locking groove (64 in FIG. 7) formed around the proximal end of syringe cylinder 60. With the seal and lock assembly 20 and needle corner base 6 anchored proximally of the syringe, the hypodermic needle 2 projects into the interior of the syringe cylinder 60 from the proximal end thereof.

Figure 15:
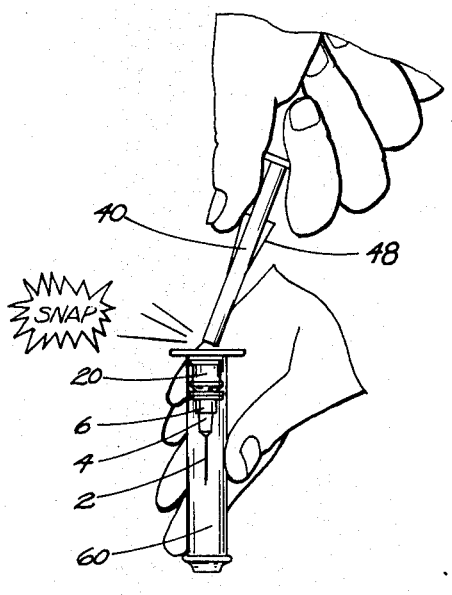

In FIG. 15, the piston assembly stem 40 is detached from the seal and lock assembly 20. More particularly, with the locking skirt of seal and lock assembly 20 anchored within the locking groove of syringe cylinder 60 such that the seal and lock assembly is positioned adjacent the open proximal end of cylinder 60, a bending force is exerted upon piston stem 40 until the locking teeth (42 in FIG. 6) thereof are snapped out of engagement with the locking slots formed in the locking skirt (34 in FIG. 4) of seal and lock assembly 20. The piston stem 40 is then removed from the syringe cylinder 60. However, the seal and lock assembly 20 continues to be retained at the proximal cylinder end to prevent access to the interior of the syringe cylinder and to the needle 2 located therewithin.

Figure 16:
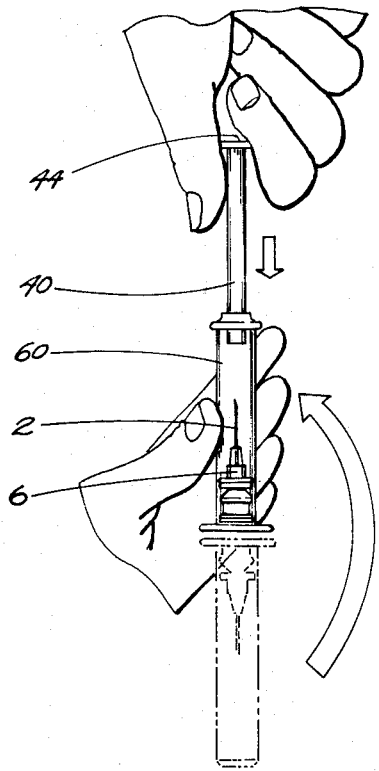

In FIG. 16, the syringe cylinder 60 is rotated around a 180 arc until an orifice of the distal bore (to which the needle carrier base 6 was formerly attached) faces upwardly. The piston stem 40 is inserted through the now open orifice at the distal cylinder end and advanced axially through the interior of the syringe cylinder 60 (in the direction of the reference arrow) toward the canula of hypodermic needle 2.

Figure 17:
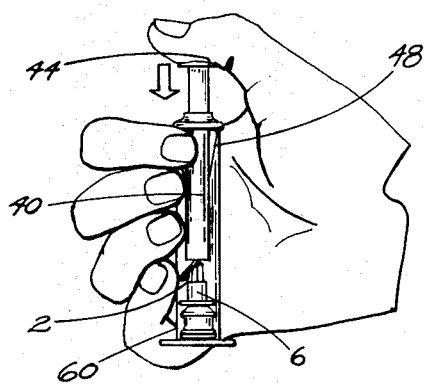

In FIG. 17, a sufficient axial force is exerted upon the stem flange 44 to force the stem 40 into contact with the needle canula at the interior of the syringe cylinder 60, such that hypodermic needle 2 is received within the tapered needle point receptacle (45 in FIG. 6) at the distal end of stem 40. The impact of needle 2 against the needle port receptacle of stem 40 automatically causes the needle to either bend or collapse axially, rather than unsafely snap, whereby to prevent explosive airborne contamination. Inserting the stem 40 through the distal cylinder end bends the flexible locking catch 48 into its surrounding recess (49 in FIG. 6). When the stem 40 impacts the canula of hypodermic needle 2 at the interior of syringe cylinder 60, the spring-like resilience of locking catch 48 causes the catch 48 to move out of its surrounding recess and into engagement with the seal surface (74 of FIG. 7) to block the withdrawal of stem 40 from cylinder 60. The stem 40 is thereby locked at its final position within the syringe cylinder to create a self-contained disposal cartridge with the needle canula destroyed, shielded and rendered irretrievable therewithin.

Thus, by virtue of the present invention, the hypodermic needle 2 is destroyed rendering an emptied syringe safe against accidental needle strikes by eliminating the need for health care workers to either handle or cut the needle as has heretofore been required with conventional syringes. Moreover, reuse of the emptied syringe for possible drug related purposes is prevented inasmuch as the hypodermic needle 2 and the needle carrier base 6 are automatically and permanently locked within the syringe, such that the needle 2 is shielded by the syringe cylinder 60. With the seal lock assembly 20 retained at one end thereof and the stem 40 retained at the opposite end.

Figure 18:
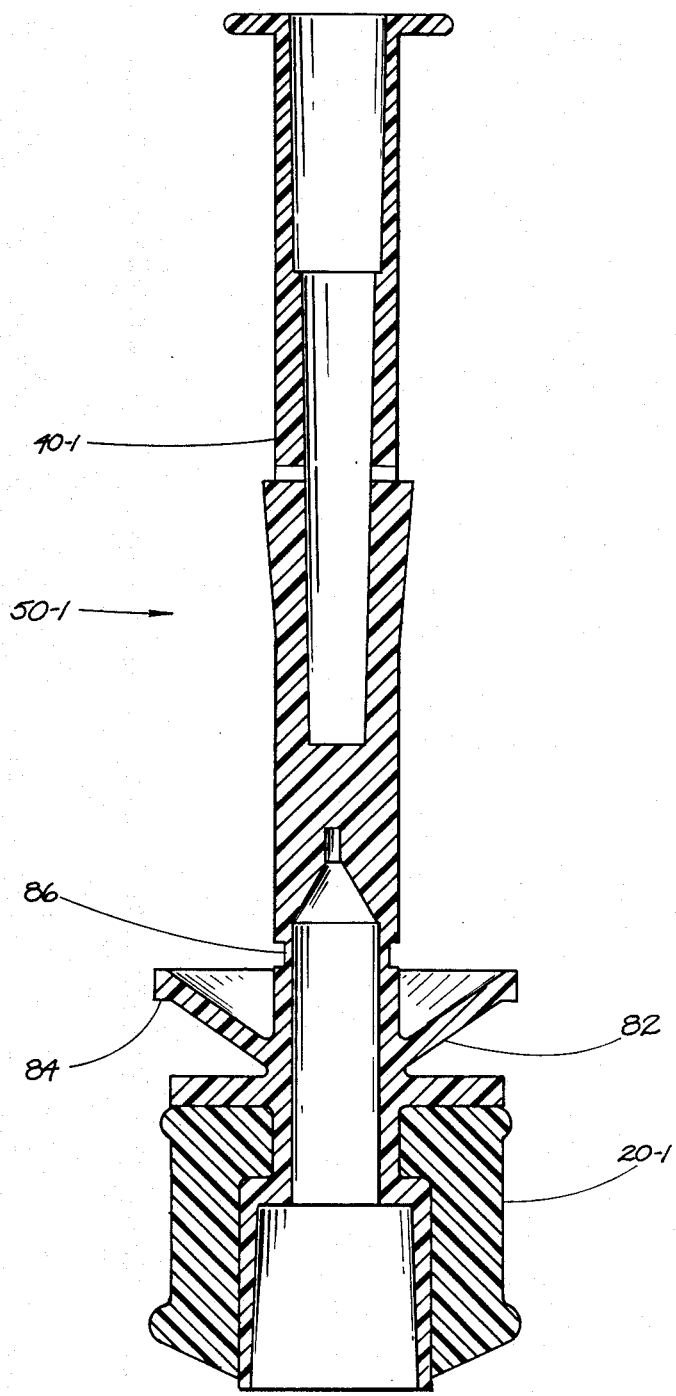
FIG. 18 shows a monolithic piston assembly which forms an alternate embodiment of the present invention.

FIG. 18 of the drawings shows an alternate monolithic piston assembly 50-1 for use in the syringe cylinder of the presently disclosed anti-needle strike and anti-drug abuse syringe. As previously disclosed, the piston assembly 50 in FIG. 2 comprises the detachable connection of a piston stem 40 to a seal and lock assembly 20. However, in FIG. 18, piston assembly 50-1 includes the integral connection of the piston stem 40-1 to the seal and lock assembly 20-1. A narrow groove 86 having a smaller diameter than that of either the piston stem or the seal and lock assembly is formed around the piston assembly 60-1 at the interface of piston stem 40-1 with seal and lock assembly 20-1. What is more, the disk-like locking skirt 34 of the seal and lock assembly 20 of FIG. 4 is replaced by a flexible, conical locking base 82. An annular flange 84 extends around the periphery of locking base 82. When the piston assembly 50-1 is moved axially through the syringe cylinder and the seal and lock assembly 20-1 is relocated from the distal to the proximal cylinder end after the syringe has been emptied, the annular flange 84 of flexible locking base 82 is received and anchored within the internal locking groove (64 in FIG. 7) of the cylinder to prevent the removal of seal and lock assembly 20-1 from the proximal cylinder end, whereby to prevent access to the interior of the syringe cylinder and to the hypodermic needle extending therein.

With the annular flange 84 anchored within the locking groove at the proximal cylinder end, a suitable bending force is applied to piston stem 40-1 to break the piston assembly 50-1 at groove 86 and, thereby, detach the stem 40-1 from seal and lock assembly 20-1. Piston stem 40-1 may then be removed from the syringe cylinder to be inserted through the distal bore end in the manner and for the purpose previously described when referring to FIGS. 16 and 17.

Figure 19:
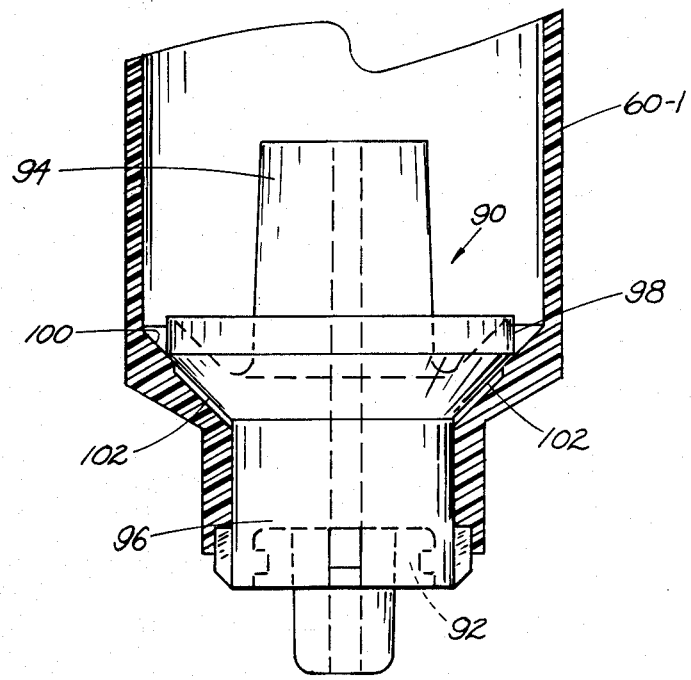
FIG. 19 shows a self-sealing needle carrier base which forms another alternate embodiment of the present invention.

In FIG. 19 of the drawings, a modified, self-sealing needle carrier base 90 is shown which eliminates the elastomeric sealing ring (designated 19 in FIG. 3). Like the needle carrier base 6 of FIG. 3, the self-sealing needle carrier base 90 includes a distal luer lock receptacle 92, a tapered proximal stem 94, and a cylindrical barrel portion 96 disposed therebetween. However, needle carrier base 90 includes a flexible, conical skirt 98 coextensively formed with and extending around barrel portion 96 at the interface of the barrel portion 96 with tapered stem 94.

The syringe cylinder 60-1 of FIG. 19 is provided with a tapered, annular internal sealing surface 100 which is located at the distal end thereof below the distal bore. The taper (e.g. approximately 60°) of sealing surface 100 corresponds with the angle of the conical skirt 98. Thus, when the needle carrier base 90 is removably attached to cylinder 60-1 within the distal bore (in the manner previously disclosed when referring to FIGS. 7-9), the flexible skirt 98 is automatically seated upon and fluid-sealed against internal sealing surface 100. A narrow groove 102 extends around the periphery of sealing surface 100. Therefore, in the assembled syringe relationship of FIG. 9, fluidic pressure applied axially through the cylinder 60-1 and against needle carrier base 90 will force the flexible skirt 98 to move into sealing engagement with the distal end of syringe cylinder 60-1 along the internal sealing surface 100. Moreover, the narrow groove 102 formed within sealing surface 100 provides a receptacle into which the flexible skirt is forced to thereby create an efficient, fluid-tight seal at the interface between the self-sealing needle base carrier 90 and syringe cylinder 60-1.

It will be apparent that while a preferred embodiment of the invention has been shown and described, various modifications and changes may be made without departing from the true spirit and scope of the invention.

Having thus set forth a preferred embodiment of the present invention, what is claimed is:

1. An anti-needle strike and anti-drug abuse syringe comprising a hollow syringe cylinder, a hypodermic needle, means for carrying said hypodermic needle to be connected to said needle and removably attached to a first end of said syringe cylinder such that said hypodermic needle projects outwardly from said first end by which to inject or infuse a fluid, means to relocate said needle carrying means from said first cylindrical end to another location within said cylinder such that said hypodermic needle extends within the interior of said syringe cylinder from said other location, and means to be inserted through said first cylinder end after the removal of said needle carrying means therefrom, said means to be inserted extending into the interior of said cylinder to prevent access to or reuse of said needle after fluid has been injected from said cylinder.

2. The syringe recited in claim 1, wherein said needle carrying means has at least one tooth extending therefrom and said syringe cylinder has at least one notch formed in the first end thereof, said tooth being received within said notch to removably attach said needle carrying means to said first cylinder end.

3. The syringe recited in claim 2, wherein the first end of said syringe cylinder has a ramp portion located adjacent to the notch formed therein, so that a rotation of said needle carrying means with the tooth thereof received in said notch causes a corresponding displacement of said tooth along said ramp and away from said notch to prevent the removal of said needle carrying means from said first cylinder end.

4. The syringe recited in claim 1, wherein the means to relocate said needle carrying means from the first end of said syringe cylinder includes a piston assembly adapted for reciprocal and axial movement through said cylinder, said piston assembly having means formed at a first end thereof to engage said needle carrying means at the first cylinder end and to remove said needle carrying means to said other location when said piston assembly is moved through said syringe cylinder and away from said first end.

5. The syringe recited in claim 4, wherein said needle carrying means includes a tapered portion and said piston assembly includes a receptacle, said receptacle dimensioned to receive the tapered portion of said needle carrying means therewithin when said piston assembly is moved to the first end of said syringe cylinder and into engagement with said needle carrying means.

6. The syringe recited in claim 5, wherein said piston assembly comprises fluid seal means having said receptacle formed therein and an elongated stem connected to said seal means, said fluid seal means and said stem being detachably connected to one another.

7. The syringe recited in claim 6, wherein said fluid seal means and said elongated stem are integrally connected together to form a monolithic piston assembly, said piston assembly having a relatively narrow area formed at the interface of said fluid seal means and said stem, said piston assembly being breakable at said relatively narrow area for detaching said stem from said seal means.

8. The syringe recited in claim 6, wherein said piston stem has a recess formed therein and said fluid seal means has at least one terminal portion extending outwardly therefrom, said terminal portion sized to be removably received within said recess in order to detachably connect said fluid seal means to said stem to form said piston assembly.

9. The syringe recited in claim 8, wherein said fluid seal means has at least one radially extending locking slot formed therein and said piston stem has at least one axially extending tooth, said axially extending tooth sized to be snapped into engagement with said radially extending slot in order to detachably connect said fluid seal means to said stem to form said piston assembly.

10. The syringe recited in claim 6, wherein said piston stem has a hollow storage chamber formed therein in which to store said hypodermic needle prior to the connection of said needle to said needle carrying means.

11. The syringe recited in claim 6, wherein the end of said syringe cylinder opposite said first cylinder end has an internal groove formed therearound and said fluid seal means has a flange to be received by said groove for anchoring said fluid seal means at said opposite end, said hypodermic needle extending within the interior of said syringe cylinder from said opposite end when said needle carrying means is relocated from said first to said other location within said cylinder.

12. The syringe recited in claim 11, wherein the means to be inserted through the first end of said cylinder and into the interior of said cylinder is said piston stem, said stem being detached from said fluid seal means and inserted through said first cylinder end and into contact with said hypodermic needle at the interior of said cylinder to destroy said needle.

13. The syringe recited in claim 12, wherein said piston stem includes a locking catch to engage the first end of said syringe cylinder and prevent the removal of said stem from said cylinder after said stem is inserted through said first cylinder end and into contact with said hypodermic needle at the interior of said cylinder.

14. An anti-needle strike and anti-drug abuse syringe comprising:
a hollow syringe cylinder;
a hypodermic needle removably connected to a first end of said cylinder and extending outwardly therefrom;
piston assembly means movable through said cylinder for causing an injection from or infusion of fluid into said cylinder, said piston assembly means having means to engage said needle at said first cylinder end and to relocate said needle from said first to the opposite end of said cylinder, such that said needle extends within the interior of said cylinder from said opposite end; and
means to be inserted through said first cylinder end after the removal of said needle therefrom, said means to be inserted extending into the interior of said cylinder to prevent access to or reuse of said needle after fluid has been injected from said cylinder.

15. The syringe recited in claim 14, further comprising needle carrying means to be connected to said hypodermic needle, said needle carrying means removably attached to said first cylinder end for removably connecting said needle thereat.

16. The syringe recited in claim 15, wherein said needle carrying means includes a tapered portion and said piston assembly means includes a receptacle, said receptacle dimensioned to receive said tapered portion therewithin for engaging the needle carrying means when said piston assembly means is moved to said first cylinder end.

17. The syringe recited in claim 16, wherein said piston assembly means comprises a plunger having said receptacle formed therein and an elongated stem connected to said plunger, said plunger and said stem being detachable from one another.

18. The syringe recited in claim 17, wherein the means to be inserted through said first cylinder end is said piston stem, said stem being detached from said plunger and inserted through said first cylinder end to impact and thereby destroy said hypodermic needle at the interior of said syringe cylinder after said piston assembly means has engaged and removed said needle and said needle carrying means from said first to said opposite cylinder end.

19. The syringe recited in claim 18, wherein said plunger and said stem are integrally connected together to form a one-piece piston assembly means, said piston assembly means having a relatively narrow area at the interface of said plunger and said stem, said piston assembly means being breakable at said relatively narrow area to detach said stem from said plunger.

20. The syringe recited in claim 18, wherein said plunger includes a flange having at least one terminal portion extending outwardly therefrom and at least one radial slot formed therein, said stem having a recess to removably receive said terminal portion and an axially extending tooth to be snapped within said radial slot in order to detachably connect said stem to said plunger to form said piston assembly means.

21. An anti-needle strike and anti-drug abuse syringe comprising:
a hollow syringe cylinder;
a hypodermic needle removably connected to a first end of said cylinder and extending outwardly therefrom; and
piston assembly means movable through said cylinder for causing an injection from or infusion of fluid into said cylinder, said piston assembly means including the detachable connection of a plunger to an elongated stem;
said plunger having means to engage said needle at said first cylinder end and to relocate said needle from said first to the opposite end of said cylinder such that said needle extends within the interior of said cylinder from said opposite end;

said stem being detached from said plunger and inserted through said first cylinder end to impact and thereby destroy said needle at the interior of said syringe cylinder after said plunger has engaged and removed said needle from said first to said opposite cylinder end.

* * * * *